US011123475B2

(12) United States Patent
Rubinsky et al.

(10) Patent No.: US 11,123,475 B2
(45) Date of Patent: *Sep. 21, 2021

(54) METHODS, SYSTEMS, AND APPARATUSES FOR TISSUE ABLATION USING ELECTROLYSIS AND PERMEABILIZATION

(71) Applicant: RM2 TECHNOLOGY LLC, Miami, FL (US)

(72) Inventors: Boris Rubinsky, El Cerrito, CA (US); Paul Mikus, Coto de Caza, CA (US); Liel Rubinsky, El Cerrito, CA (US)

(73) Assignee: RM2 TECHNOLOGY LLC, Miami, FL (US)

( * ) Notice: Subject to any disclaimer, the term of this patent is extended or adjusted under 35 U.S.C. 154(b) by 135 days.

This patent is subject to a terminal disclaimer.

(21) Appl. No.: 16/509,416

(22) Filed: Jul. 11, 2019

(65) Prior Publication Data

US 2019/0357960 A1 Nov. 28, 2019

Related U.S. Application Data

(63) Continuation of application No. 15/036,393, filed as application No. PCT/US2014/065794 on Nov. 14, 2014, now Pat. No. 10,390,874.

(Continued)

(51) Int. Cl.
*A61B 18/14* (2006.01)
*A61M 1/00* (2006.01)
(Continued)

(52) U.S. Cl.
CPC .............. *A61M 1/90* (2021.05); *A61B 18/02* (2013.01); *A61B 18/04* (2013.01); *A61B 18/12* (2013.01);
(Continued)

(58) Field of Classification Search
CPC ......... A61B 18/02; A61B 18/04; A61B 18/12; A61B 18/1492; A61B 18/16;
(Continued)

(56) References Cited

U.S. PATENT DOCUMENTS 5,389,069 A 2/1995 Weaver
5,468,223 A 11/1995 Mir
(Continued)

FOREIGN PATENT DOCUMENTS

EP 2425871 A2 3/2012
EP 1696812 B1 7/2015
(Continued)

OTHER PUBLICATIONS

Examination Report dated Mar. 19, 2018 for European Application No. 14862589.0.
(Continued)

*Primary Examiner* — Michael F Peffley
(74) *Attorney, Agent, or Firm* — Dorsey & Whitney LLP

(57) ABSTRACT

Example apparatuses and systems are disclosed for providing controlled delivery of electrolysis treatment and cellular permeabilization treatment to a site in tissue. A system disclosed may include an electrode, a power supply, and a controller. The controller may control a charge applied to the electrode to induce a direct current through the aqueous matrix to produce electrolysis products and a voltage to produce electroporation. The duration and magnitude of the charge applied may determine the dose of the products and the degree of the permeabilization of cells in the treatment site. The composition of the electrodes may be chosen in accordance with the desired products produced and electroporation effects. An apparatus is disclosed that may be in the form of electrodes for electrolysis and electrodes for
(Continued)

electroporation applied to the tissue. An apparatus is disclosed that may be used for treating internal tissue.

24 Claims, 7 Drawing Sheets

Related U.S. Application Data

(60) Provisional application No. 61/904,142, filed on Nov. 14, 2013, provisional application No. 61/921,084, filed on Dec. 27, 2013, provisional application No. 61/938,623, filed on Feb. 11, 2014.

(51) Int. Cl.
| | |
|---|---|
| C25B 1/26 | (2006.01) |
| C25B 11/04 | (2021.01) |
| C25B 9/17 | (2021.01) |
| A61M 25/10 | (2013.01) |
| A61N 1/05 | (2006.01) |
| A61N 1/32 | (2006.01) |
| A61B 18/02 | (2006.01) |
| A61B 18/04 | (2006.01) |
| A61B 18/12 | (2006.01) |
| A61B 18/00 | (2006.01) |
| A61B 18/16 | (2006.01) |

(52) U.S. Cl.
CPC ....... *A61B 18/1492* (2013.01); *A61M 25/104* (2013.01); *A61N 1/0502* (2013.01); *A61N 1/32* (2013.01); *A61N 1/325* (2013.01); *A61N 1/327* (2013.01); *C25B 1/26* (2013.01); *C25B 9/17* (2021.01); *C25B 11/04* (2013.01); *A61B 18/16* (2013.01); *A61B 2018/00333* (2013.01); *A61B 2018/00404* (2013.01); *A61B 2018/00434* (2013.01); *A61B 2018/00452* (2013.01); *A61B 2018/00464* (2013.01); *A61B 2018/00482* (2013.01); *A61B 2018/00517* (2013.01); *A61B 2018/00547* (2013.01); *A61B 2018/00577* (2013.01); *A61B 2018/00613* (2013.01); *A61B 2018/00827* (2013.01); *A61B 2018/00892* (2013.01); *A61B 2018/143* (2013.01); *A61B 2018/1425* (2013.01); *A61M 2025/105* (2013.01); *A61M 2025/1052* (2013.01); *A61M 2205/054* (2013.01); *A61M 2205/52* (2013.01)

(58) Field of Classification Search
CPC .......... A61B 2018/00333; A61B 2018/00404; A61B 2018/00434; A61B 2018/00452; A61B 2018/00464; A61B 2018/00482; A61B 2018/00517; A61B 2018/00547; A61B 2018/00577; A61B 2018/00613; A61B 2018/00827; A61B 2018/00892; A61B 2018/00994; A61B 2018/1266; A61B 2018/1425; A61B 2018/143; A61B 2018/1472; A61M 1/0088; A61M 2025/105; A61M 2025/1052; A61M 2205/054; A61M 2205/52; A61M 25/104; C25B 11/04; C25B 1/26; C25B 9/17; A61N 1/0502; A61N 1/205; A61N 1/32; A61N 1/325; A61N 1/327
See application file for complete search history.

(56) References Cited

U.S. PATENT DOCUMENTS

| | | | |
|---|---|---|---|
| 5,911,223 A * | 6/1999 | Weaver | A61N 1/0424 |
| | | | 128/898 |
| 6,300,108 B1 | 10/2001 | Rubinsky et al. | |
| 6,366,808 B1 | 4/2002 | Schroeppel et al. | |
| 6,403,348 B1 | 6/2002 | Rubinsky et al. | |
| 7,113,821 B1 | 9/2006 | Sun et al. | |
| 7,344,533 B2 | 3/2008 | Pearson et al. | |
| 7,680,543 B2 | 3/2010 | Azure | |
| 7,718,409 B2 | 5/2010 | Rubinsky et al. | |
| 7,955,827 B2 | 6/2011 | Rubinsky et al. | |
| 8,048,067 B2 | 11/2011 | Davalos et al. | |
| 8,145,316 B2 | 3/2012 | Deem et al. | |
| 8,282,631 B2 | 10/2012 | Davalos et al. | |
| 8,926,606 B2 | 1/2015 | Davalos et al. | |
| 9,005,189 B2 | 4/2015 | Davalos et al. | |
| 9,283,051 B2 | 3/2016 | Garcia et al. | |
| 9,700,368 B2 | 7/2017 | Callas et al. | |
| 9,901,735 B1 * | 2/2018 | Lee | A61N 1/36025 |
| 10,154,873 B2 | 12/2018 | Rubinsky et al. | |
| 10,390,874 B2 | 8/2019 | Rubinsky et al. | |
| 2001/0021868 A1 | 9/2001 | Herbst et al. | |
| 2002/0010491 A1 | 1/2002 | Schoenbach et al. | |
| 2003/0042134 A1 | 3/2003 | Tremblay | |
| 2004/0213698 A1 | 10/2004 | Tennakoon et al. | |
| 2006/0116663 A1 | 6/2006 | Joshi et al. | |
| 2008/0167650 A1 * | 7/2008 | Joshi | C01B 13/10 |
| | | | 606/41 |
| 2009/0287208 A1 | 11/2009 | Rosemberg | |
| 2010/0030211 A1 | 2/2010 | Davalos et al. | |
| 2010/0036446 A9 | 2/2010 | Auge et al. | |
| 2010/0168646 A1 | 7/2010 | Greenbaum et al. | |
| 2010/0183745 A1 | 7/2010 | Rossi et al. | |
| 2012/0059255 A1 * | 3/2012 | Paul | A61B 18/14 |
| | | | 600/431 |
| 2012/0071874 A1 | 3/2012 | Davalos et al. | |
| 2012/0130369 A1 | 5/2012 | Cadossi et al. | |
| 2012/0150173 A1 | 6/2012 | Joshi et al. | |
| 2012/0220998 A1 * | 8/2012 | Long | A61B 18/1206 |
| | | | 606/41 |
| 2013/0218157 A1 | 8/2013 | Callas et al. | |
| 2014/0066913 A1 | 3/2014 | Sherman | |
| 2014/0316485 A1 | 10/2014 | Ackermann et al. | |
| 2016/0184003 A1 * | 6/2016 | Srimathveeravalli | ....................... |
| | | | A61B 18/1206 |
| | | | 606/39 |
| 2016/0287867 A1 | 10/2016 | Rubinsky et al. | |
| 2016/0296269 A1 | 10/2016 | Rubinsky et al. | |
| 2018/0193082 A1 | 7/2018 | Rubinsky et al. | |
| 2019/0117291 A1 | 4/2019 | Rubinsky et al. | |

FOREIGN PATENT DOCUMENTS

| | | |
|---|---|---|
| WO | 03103521 A1 | 12/2003 |
| WO | 2007070637 A2 | 6/2007 |
| WO | 2015021113 A1 | 2/2015 |
| WO | 2015073877 A1 | 5/2015 |
| WO | 2015073885 A1 | 5/2015 |
| WO | 2016178697 A1 | 11/2016 |

OTHER PUBLICATIONS

International Search Report and Written Opinion dated Apr. 21, 2015 received for PCT/US2014/065794.
Receipt of extended EP search report for application No. 14862589.0 dated May 10, 2017.
Ivorra, et al., "Electric Field Modulation in Tissue Electroporation With Electrolytic and Non-Electrolyic Additives", Bioelectrochemistry 70, Feb. 2007, pp. 551-560.
Ivorra, et al., "In Vivo Electrical Impedance Measurements During and After Electroporation of Rat Liver", Bioelectrochemistry 70, Oct. 2006, pp. 287-295.
Office Action for EP Application No. 14862589.0, dated Dec. 11, 2020.

(56) References Cited

OTHER PUBLICATIONS

Mir, et al., "Mechanisms of Electrochemotherapy", Advanced Drug Delivery Reviews, vol. 35, No. 1, Jan. 1, 1999, XP055754391, Amsterdam, NL, pp. 107-118.
U.S. Appl. No. 17/195,298 titled "Methods, Systems, and Apparatuses for Tissue Ablation Using Pulse Shape Designs" filed Mar. 8, 2021.

* cited by examiner

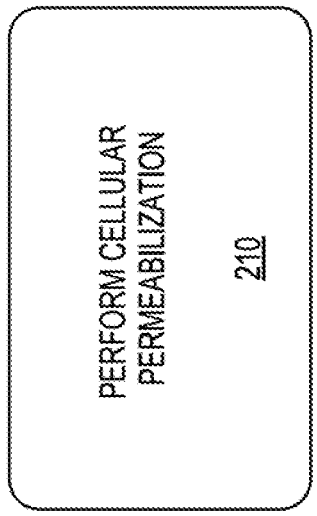
Fig. 2A
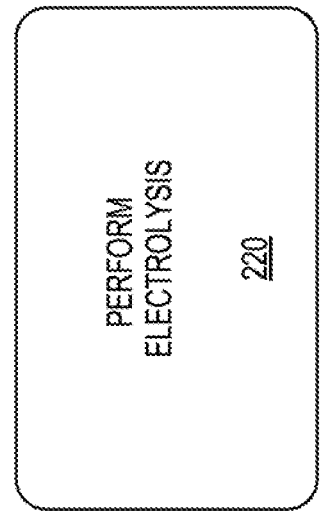
Fig. 2B

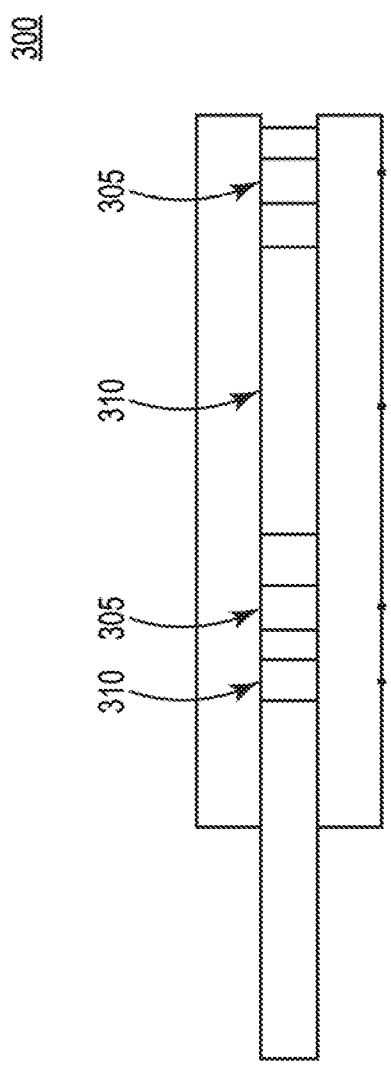

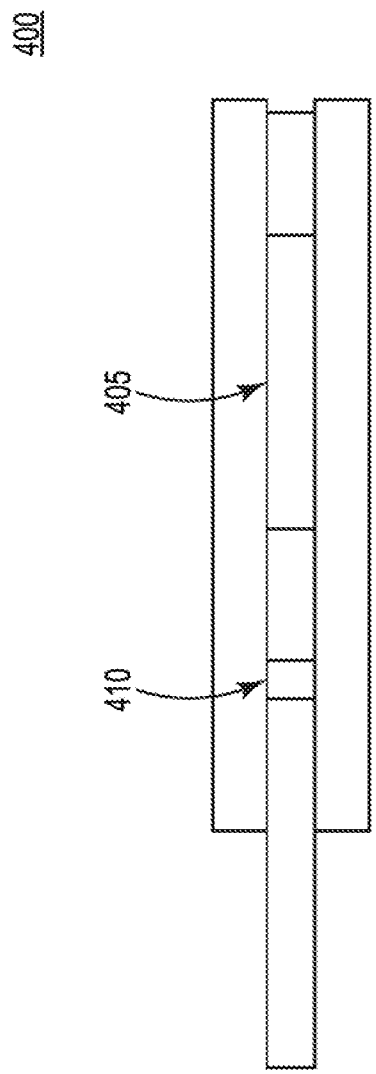

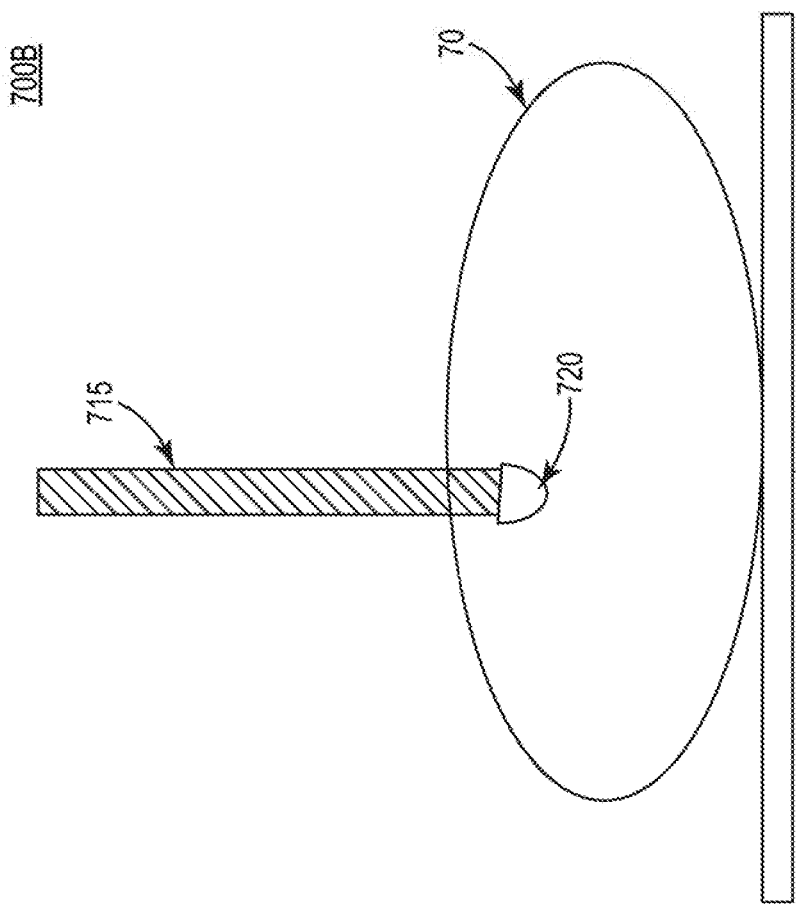
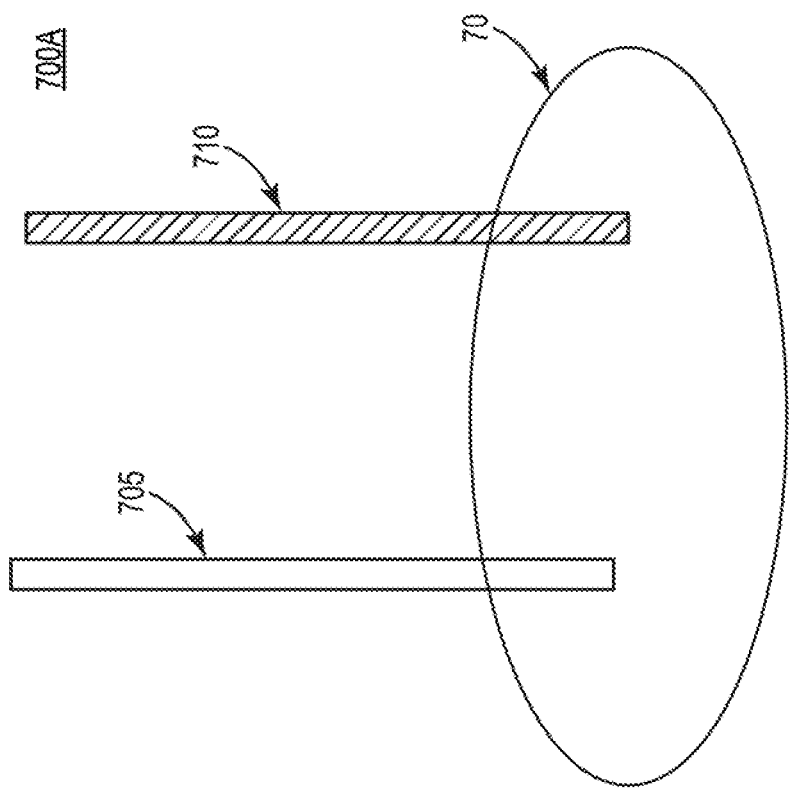
Fig. 5A
Fig. 5B

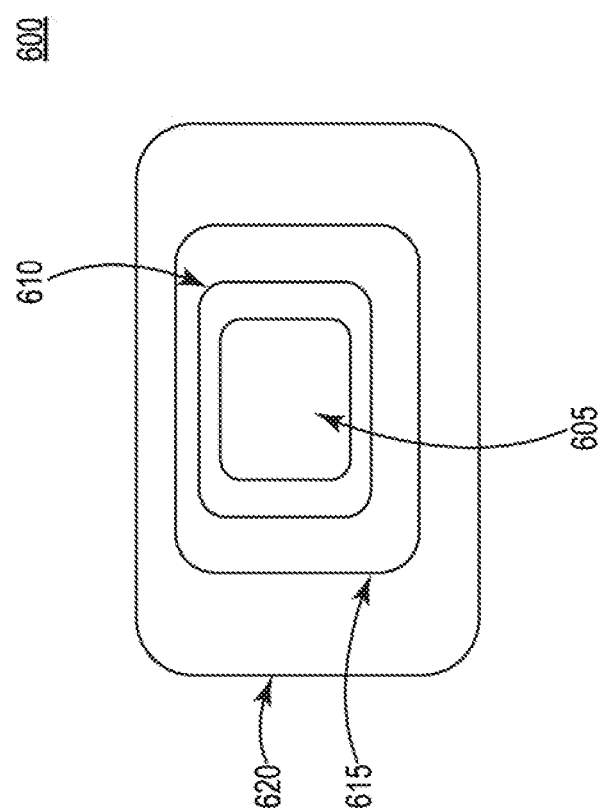

METHODS, SYSTEMS, AND APPARATUSES FOR TISSUE ABLATION USING ELECTROLYSIS AND PERMEABILIZATION

CROSS-REFERENCE TO RELATED APPLICATIONS

This application is a continuation of U.S. patent application Ser. No. 15/036,393 filed May 12, 2016, which is a U.S. national stage application of PCT Application No. PCT/US2014/065794 filed Nov. 14, 2014, which claims priority to provisional application Ser. No. 61/904,142 filed on Nov. 14, 2013, U.S. Ser. No. 61/921,084 filed on Dec. 27, 2013, and U.S. Ser. No. 61/938,623 filed on Feb. 11, 2014.

The entire disclosures of the afore-mentioned applications are considered to be part of the disclosure of the instant application and are hereby incorporated by reference in their entirety for any purpose.

BACKGROUND

Electrolysis has been used for minimally invasive tissue ablation since the early 1800's. The process of electrolysis occurs at the electrode surfaces for electrodes submerged in an ionic conducting media. New chemical species are generated at the interface of the electrodes as a result of the electric potential driven transfer between electrons and ions or atoms. The various chemical species produced near the electrodes diffuse away in a process driven by differences in electrochemical potential. In physiological solutions these chemical reactions also yield changes in pH, resulting in an acidic region near the anode and a basic region near the cathode. Tissue ablation is driven by two factors: a cytotoxic environment developing due to local changes in pH, as well as the presence of some of the new chemical species formed during electrolysis. Electrolysis is a chemical ablation mechanism, and the extent of ablation is a function of the concentration of the chemical species and the exposure time to these chemicals. The total amount of electrolytic products generated during electrolysis is related to the charge delivered during the process, and therefore the total charge is used as a quantitative measure for the extent of electrolysis.

Over the last two decades, substantial research has been done on tissue ablation by products of the electrolysis process in ionic aqueous solutions, including cell and animal experiments, mathematical modeling, and clinical work. In the contemporary literature, electrolytic ablation using products of electrolysis generated from tissue ions and molecules is sometimes referred to as Electro-Chemical Therapy (EChT). Unless specifically stated otherwise, the terms "the products of electrolysis" and "electrolysis products" refer to products generated from the transfer and removal of electrons to ions and molecules in an ionic aqueous solution and involve only the components of the aqueous solution or tissue as an aqueous solution. Unless stated otherwise, the process of electrolysis implies the use of inert electrodes that do not participate in the process of electrolysis except as a source or sink of electrons or as catalysts. This is also how electrolysis is defined in EChT. As used herein, "electrolysis" or "electrolytic" refers to the process of electrolysis and the products of electrolysis as defined above. Electrolytic ablation has been shown to exhibit several unique attributes. First, due to live chemical nature of the ablation process, the diffusion of chemical species in the tissue and the rate of chemical reactions dominate the time scale of the procedure. Second, the chemical products at the anode differ from those formed at the cathode, thus resulting in distinct mechanisms of ablation. Finally, electro-osmotic forces drive the migration of water from the anode to the cathode, further magnifying the contrasting physiological effects at the electrode surfaces. From an operational standpoint, electrolysis may use very low voltages and currents, providing advantages relative to other ablation techniques, e.g. reduced instrumentation complexity. It is, however, a lengthy procedure, controlled by the process of diffusion and the need for high concentrations of electrolytically-produced ablative chemical species.

Electroporation also harnesses an electricity-induced phenomenon; it differs from electrolysis by employing a different set of biophysical principles. The bioelectric phenomenon of electroporation is characterized by the permeabilization of the cell membrane through the application of very brief, high-magnitude electric field pulses. The extent of membrane permeabilization is a function of the electric field strength. Electroporation can be used to produce reversible pores, defects, in the lipid bilayer, allowing for the introduction of molecules such as genes and drugs into cells. This is generally referred to as "reversible electroporation" The electric parameters, however, can be designed to produce irreversible defects in the cell membrane, resulting in a cell membrane that does not reseal after the field is removed. This is referred to as "irreversible electroporation". Reversible electroporation techniques have been combined with anticancer drugs such as bleomycin to target cancerous tissues for successful clinical use in the field of electrochemotherapy. Reversible electroporation is also used in other medical and biotechnological applications, including transfection and introduction of molecules such as siRNA into cells that survive the permeabilization process. Electroporation specifically targets the cell membrane through the application of an electric field that develops instantaneously. Irreversible electroporation may be used for tissue ablation.

SUMMARY

An example method for targeted tissue ablation may include permeabilizing cell membranes in the targeted tissue and delivering electrolysis products to the targeted tissue, wherein the electrolysis products may be toxic to the cells in the tissue.

An example apparatus for tissue ablation may include a source of electrolysis products, wherein the source of electrolysis products may be positioned proximal the targeted tissue and a device that may be configured to permeabilize cell membranes in the targeted tissue.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several examples in accordance with the disclosure and are, therefore, not to be considered limiting of its scope, the disclosure will be described with additional specificity and detail through use of the accompanying drawings, in which

FIG. 2A is a flow chart illustrating a method according to an embodiment of the disclosure.

FIG. 2B is a flow chart illustrating a method according to an embodiment of the disclosure.

FIG. 3 is a schematic diagram of a treatment probe according to an embodiment of the disclosure.

FIG. 4 is a schematic diagram of a treatment probe according to an embodiment of the disclosure.

FIG. 5A illustrates an electrode configurations according to an embodiment of the disclosure.

FIG. 5B illustrates an electrode configuration according to an embodiments of the disclosure.

FIG. 7 is a schematic illustration of an electrolysis device according to an embodiment of the disclosure.

DETAILED DESCRIPTION

Figure 1:
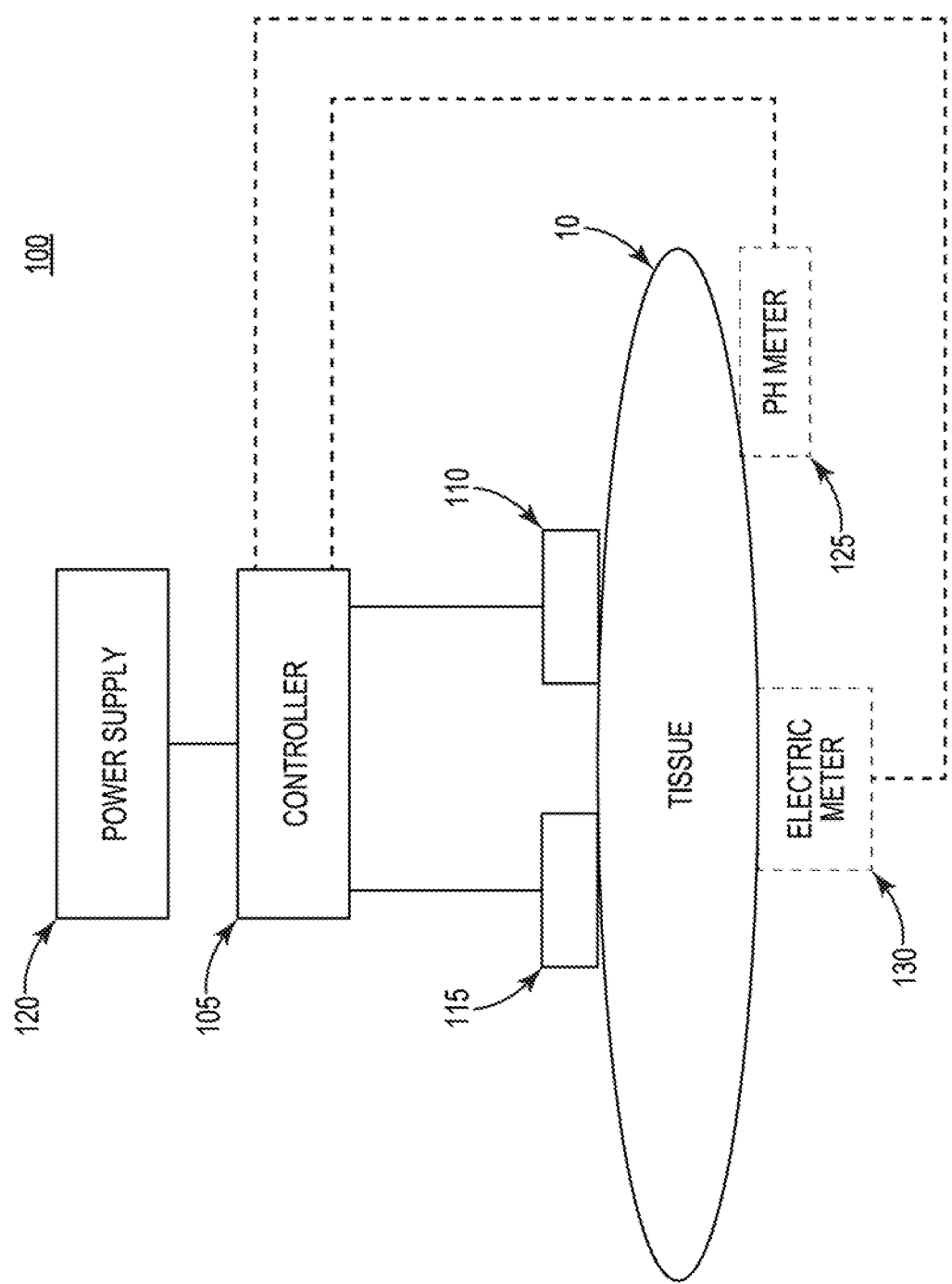
FIG. 1 is a schematic illustration of an electrolysis system according to an embodiment of the disclosure.

Certain details are set forth below to provide a sufficient understanding of embodiments of the disclosure. However, it will be clear to one skilled in the art that embodiments of the disclosure may be practiced without these particular details. Moreover, the particular embodiments of the present disclosure described herein are provided by way of example and should not be used to limit the scope of the invention to these particular embodiments. In other instances, well-known materials, components, processes, controller components, software, circuitry, timing diagrams, and/or anatomy have not been described or shown in detail in order to avoid unnecessarily obscuring the embodiments.

This disclosure describes the combined effect of electroporation with electrolysis which may allow for more effective ablation of tissue. Combining electroporation with electrolysis may produce a substantial increase in the extent of tissue ablation as compared to the ablation produced by the same dose of electrolysis or electroporation separately. Without being bound by a particular theory, this phenomenon may be attributed to the electrolytically produced chemicals that may pass through a permeabilized cell membrane into the interior of the cell, thereby causing cell damage at much lower concentrations of electrolytic products than for intact cells. This mechanism of tissue ablation may be affected by the dose of chemical species produced by electrolysis at the electrodes, the process of electro-osmotic diffusion from the electrodes into tissue and the permeabilization of the cell membrane in the targeted tissue.

Electrolysis generally refers to a process of inducing an electrochemical reaction that involves passing a direct current through an ionic solution via two electrodes. Electrolysis may facilitate live removal and/or addition of electrons from atoms and/or ions, which may lead to the formation of new products. For example, by passing a DC current through a saline solution (NaCl and $H_2O$), hypochlorous acid (HClO) may be formed. The products formed may be based, at least in part, on the ionic composition of the solution, pH, and/or materials included in the electrodes. The amount of electrolysis products formed may be based at least in part on the magnitude of the current and/or the duration the current is applied. The current may be generated by coupling a power source to the electrodes. Examples of power sources may include, but are not limited to, one or more, electrical network, batteries, a computer (e.g., coupled via USB cable), a solar cell, and combinations thereof.

Electrolysis products may be used for sterilization and/or ablation of tissue. Some electrolysis products, which may be generated from the ions and molecules of the aqueous solution, such as hypochlorous acid previously mentioned, may be toxic to cells and/or organisms. Hypochlorous acid and other electrolysis products may be introduced to a tissue by pouring or injecting a solution including the electrolysis products to a targeted tissue. However, electrolysis products degrade rapidly over time, reducing their effectiveness. In tissue ablation by products of electrolysis applications, it may be desired to produce the electrolysis products at the tissue site.

Electrodes for performing electrolysis may be placed in contact with a tissue or a solution in contact with the tissue. It may be advantageous to use inert electrodes, because the products of electrolysis are specifically defined from the composition of the solution. When the electrodes are activated, electrolysis products may form from the ions and molecules in the tissue and/or solution and diffuse throughout the target volume of tissue. Cells within the target site may be ablated. Electrolysis may be used in combination with other treatments such as thermal ablation, cryotherapy, cellular permeabilization, and/or combinations thereof. The permeabilization of cells may increase the diffusion of electrolysis products into the cells of the target volume of tissue. This may enhance the effectiveness of electrolysis therapy and/or reduce the amount of electrolysis products required to achieve a desired effect.

In some embodiments, electrolysis may be used in combination with electroporation and/or other cellular permeabilization treatment. The combination treatment may be more effective at ablation and/or sterilization than the individual treatments used alone. The combination of electrolysis with another treatment may generally be referred to as "multimodality electrolysis" herein.

An example method of tissue ablation through the delivery of products of electrolysis to a targeted volume of tissue, in combination with the permeabilizing of the cell membrane of the cells in targeted volume of tissue may include: bringing electrode needles to the proximity of the targeted volume of tissue, delivering electric potential to the electrodes to generate electric fields that permeabilize the cell membrane in the targeted volume of tissue, delivering electric current to the electrodes for generating the electrolytic products at the electrodes at an amount sufficient to ablate permeabilized cells in the targeted volume of tissue, and electro-osmotic diffusion of the electrolytic products throughout the targeted volume of tissue. Permeabilization and production of electrolytic products may be done in any sequence that achieves the goal of bringing the products to the cells in the targeted volume of tissue and at the same time permeabilizing these cells, such as permeabilizing the volume of cells in tissue first and generating the required amount of products of electrolysis next, generating the amount of electrolytic products first and permeabilizing the cell membrane next, simultaneously permeabilizing the cell membrane and producing the products of electrolysis, or any combination of these.

FIG. 1 is a schematic illustration of a multimodality electrolysis system 100 according to an embodiment of the disclosure. The multimodality electrolysis system 100 may be capable of performing electrolysis and at least one other treatment, such as cellular permeabilization treatment. Although the system 100 in FIG. 1 is shown on the surface of a tissue 10, the system 100 may be configured to be used inside tissue 10, proximate tissue 10, and/or in a cavity formed by tissue 10 in some embodiments. In some embodiments, the system 100 may include a controller 105 coupled to an electrolysis device 110 and a cellular permeabilization device 115. Although shown as separate devices in some embodiments the electrolysis device 110 and the cellular permeabilization device 115 may be the same device. The devices 110, 115 may be placed proximate to a treatment site on issue 10.

The controller 105 may control the timing, strength, and duration of treatments provided by the devices 110, 115. The controller 105 may, for example, be programmed to provide an electronic signal to the devices 110, 115. The electronic signal may be indicative of a dose of treatment, for example, a dose of electrolysis products. The electronic signal may control the timing and magnitude of a current generated by the electrolysis device 110 and or the cellular permeabilization device 115, which may be implemented as an electroporation device. This may allow a user to customize treatment of the tissue 10. In some embodiments, the controller is coupled to a power supply 120. In some embodiments, the power supply 120 may be included in device 110 and or device 115. In some embodiments, the power supply 120 is integrated with controller 105.

Although shown as a separate component coupled to the devices 110, 115, in some embodiments, the controller 105 may be integrated into one or both devices 110, 115 and or packaged together with one or both devices 110, 115. In some embodiments, the controller 105 may include a programmable chip coupled to the devices 110, 115. Some embodiments, the controller 105 may be implemented using a computing device (not shown) and be remotely coupled to the devices 110, 115. The computing device may be implemented using, for example, a microprocessor, a desktop, laptop, server, handheld device, a personal computer, a tablet computer, and/or a smart phone. In some examples, the computing device may be integrated with and/or shared with another piece of medical equipment. The controller 105 may be coupled by a wire or communicate with the devices 110, 115 wirelessly. In some embodiments, two separate controllers may be used in system 100. Each controller may be coupled to one of the devices 110, 115.

In some embodiments, the controller 105 may be programmed to provide an electronic signal indicative of a dose of the electrolysis products and/or a permeability level of cells. The controller 105 may, for example, include such a program, or include one or more processing devices (e.g. processors) coupled to a memory encoded with executable instructions for electrolysis treatment and at least one other treatment, such as cellular permeabilization treatment.

The system 100 may further include one or more sensors for measurement of pH 125, electric field strength 130, and/or other properties of the tissue 10. For example, the sensor may sense pH near the electrolysis device 110 and provide the pH value to the controller 105. The controller 105 may further be programmed to adjust an electronic signal provided to the electrolysis device 110 based on the pH near the device. A reservoir (not shown) may be provided for addition of compounds, such as buffers or other solutions, to the aqueous matrix to adjust the pH. In another example the pH sensor 125, may be inserted at the outer edge of the targeted volume of tissue to detect when the pH at the site has reached a desired level which may ensure the ablation of tissue at that site. This may be used as an indicator by the controller 105 to stop the electrolysis process. In another example the pH sensor 125, may be inserted at a particular site in tissue to detect when the pH at the site is reaching a potentially damaging value to avoid tissue damage at that site. This may be used as an indicator by the controller to stop the electrolysis process. In some examples the electric meter 130 may be set at a particular location in tissue to measure isoelectric field levels which may ensure that the cells at that location are permeabilized. The electric meter 130 may be implemented as an electrical conductivity meter.

In some embodiments, the electrolysis device 110 includes one or more electrodes for conducting a current through a solution. The solution may be native to the treatment site and/or it may be introduced to the treatment site. In same embodiments, the electrolysis device 110 includes an aqueous matrix in contact with the electrodes for placement proximate the treatment site. In some embodiments, the aqueous matrix may be a gel including a saline solution. In some embodiments the saline solution may be at a pH of between 3 and 5, such as a pH of 4. In some embodiments, the electrolysis device 110 may be a treatment pad for surface treatments. In some embodiments, the electrolysis device 110 may include needle electrodes and/or a catheter for use within cavities and/or tissues.

The cellular permeabilization device 115 may perform reversible and/or irreversible permeabilization. In some embodiments, the cellular permeabilization device 115 is an electroporation device. The electroporation device may include one or more electrodes for generating a potential difference across tissue for permeabilizing cells. The permeability of the cells and/or the reversibility of the permeabilization may be based, at least in part, on the magnitude of the local electric field in tissue and/or duration of the electroporation treatment. In some embodiments, the cellular permeabilization device 115 is a sonoporation device, which may use ultrasound for permeabilization device. In some embodiments, the cellular permeabilization device 115 may implement another permeabilization method such as, but not limited to, cryosurgery, freezing, coldporation, heatporation, and chemoporation.

In some embodiments, electrolysis device 110 may be packaged with the cellular permeabilization device 115. In some embodiments, the electrolysis device 110 and cellular permeabilization device 115 may be a single device. For example, the electrodes for performing electrolysis may also be used for performing electroporation.

In some embodiments the combination electrolysis and permeabilization may be combined with other modalities for tissue treatment such as thermal ablation, radiation, chemical ablation, and/or gene therapy.

FIGS. 2A and 2B are flow charts illustrating methods 200A, 200B according to embodiments of the disclosure. In some embodiments, a multimodality electrolysis system, device, and/or apparatus may be placed for treatment of a target site, for example, a tissue. The multimodality electrolysis system such as the system 100 illustrated in FIG. 1 may be used. The treatments performed by the multimodality electrolysis system may be manually controlled by a user or may be controlled by a controller, for example, controller 105 shown in FIG. 1. Generally, delivery of electrolysis products may be performed before, during, or after permeabilizing cells in a tissue to be treated. As described herein, in some examples, permeabilizing the cells before, during, and/or after delivery of the electrolysis products may improve the effectiveness of the electrolysis products in ablating the tissue.

In method 200A, electrolysis is performed at Block 205. The electrolysis may deliver electrolysis products to the target site. Electrolysis may be followed by cellular permeabilization at Block 210. Cells at the target site may have increased permeability in response to the cellular permeabilization, which may enhance delivery of the electrolysis products. Although not shown, Block 205 may be repeated after Block 210 in some embodiments. In some embodiments, Blocks 205 and 210 may be repeated in an alternating fashion for a desired period of time. Blocks 205 and 210 may be of different time durations, magnitudes, and/or other differing parameters. In some embodiments, Blocks 205 and 210 may be separated by a period of time where no treatment is applied to the target site.

In method 200B, cellular permeabilization is performed at Block 215. Cells at the target site may have increased permeability in response to the cellular permeabilization. Electrolysis may be performed following cellular permeabilization at Block 220. The electrolysis may deliver electrolysis products to the target site. Although not shown, Block 215 may be repeated after Block 220 in some embodiments. In some embodiments, Blocks 215 and 220 may be repeated in an alternating fashion for a desired period of time. Blocks 215 and 220 may be of different time durations, magnitudes, and/or other differing parameters. In some embodiments, Blocks 215 and 220 may be separated by a period of time where no treatment is applied to the target site.

In some embodiments, electrolysis and cellular permeabilization may be performed at the same time or partially at the same time. For example, current to generate electrolysis products may be provided during a same period of time as an electric field for electroporation, or current as a thermal source for permeabilizing cell membranes is applied to the tissue. In some embodiments, electrolysis and cellular permeabilization may both be performed together for a continuous period of time or intermittently. In some embodiments, one treatment may be performed continuously while the other treatment is performed intermittently. The magnitude and duration of each treatment may be modulated independently of the other treatment. For example, electrolysis may be performed continuously for several minutes while cellular permeabilization may be performed for several seconds each minute. The electrolysis may be discontinued while the cellular permeabilization continues to be performed. Other combinations of treatments may be possible. The time, duration, and order of the treatments may be chosen based at least in part on the desired effect on the target site, the size of the target site, and/or local physiological conditions of the target site.

In some embodiments, electrodes may be included on and/or in a treatment probe which may produce one of, or both electrolysis and electroporation treatment. For example, the treatment probe may be used to execute the methods described above and/or illustrated in FIGS. 2A-B. In some embodiments, the treatment probe may be used to implement an electrolysis device and/or an electroporation device, such as devices 110, 115 illustrated in FIG. 1. In some embodiments, the treatment probe may be a combination device used to implement both devices 110, 115. The treatment probe may be implemented using a point, needle, a wire, a pad, a disk, and/or combinations thereof. In some embodiments, the electrode or electrodes may include the entire treatment probe. In some embodiments, the electrode or electrodes may be included as a portion of the treatment probe.

FIG. 3 is a schematic diagram of a treatment probe 300 according to an embodiment of the disclosure. The treatment probe 300 may incorporate both electroporation electrodes 305 and electrolysis electrodes 310. The electrodes for electroporation 305 may be separate from the electrodes for electrolysis 310. Having separate electrodes for each treatment modality may allow for independent optimization of the electrode configuration for both electroporation and electrolysis. For example, the electrode design for electrolysis may include materials that are selected for specific electrolysis product species production, such as Ti coated with IrO to favor production of hypochlorous acid. The electrode material for electroporation may be selected to avoid electrolysis product formation that may result in bubble formation, which may lead to arcing. The electrodes may be in any number, size and shape of electrodes using a separate electrode delivery approach.

FIG. 4 is a schematic diagram of a treatment probe 400 according to an embodiment of the disclosure. In some embodiments, a treatment probe may integrate the electrodes 405, 410 for electrolysis and electroporation. The electrodes for electrolysis, or certain ones of the electrodes, may be the same electrodes, or certain ones of the electrodes, that deliver electroporation. The electrodes may be in any number, size and shape using an integrated electrode approach. A number of different configurations mays be used to integrate the delivery of electroporation and electrolysis into a catheter. The size, shape and configuration of the electrodes may be specifically tailored to the targeted treatment site.

In some embodiments, a treatment probe may include a combination of electrodes used for both electrolysis and electroporation delivery. For example, an electrode may be used for both electroporation and electrolysis. A separate electrode may be used to complete the electroporation delivery and a separate electrode may be used to complete the electrolysis delivery. In some embodiments, the electrodes may be included on a plurality of treatment probes. For example, a first probe may include the electrolysis anode and a second probe may include the electrolysis cathode. The first and second probes may further include electroporation electrodes. Other examples of electrode combinations include, but are not limited to, two point electrodes, one point and one needle electrode, one point electrode and one pad electrode, two monopolar needle electrodes; one bipolar needle, one multipolar needle; two surface electrodes; one surface and one needle electrode, and/or combinations thereof. Other configurations of electrodes on one or more treatment probes may also be possible. The spacing between electrodes on the treatment probe and/or the spacing between treatment probes may also be adjusted to achieve a desired electrolysis and/or electroporation effect.

FIGS. 5A-B illustrate two examples of electrode configurations 700A-B according to embodiments of the disclosure. FIG. 5A illustrates two needle electrodes 705, 710 inserted in a tissue 70. FIG. 5B illustrates a point electrode 720 on an insulated shaft 715 inserted in a tissue 70. A pad electrode 725 is placed remotely from the point electrode 720. In some embodiments, the point electrode 720 may be an anode and the pad electrode 725 may be a cathode. The examples shown in FIG. 5A-B are for illustrative purposes only, and other electrode configurations are possible.

In some embodiments, one or more treatment probes and/or electrodes may be integrated into a catheter. The catheter may include one or more lumens. Each lumen may include one or more treatment probes. The electrodes for delivering the treatments may be in any combination, shape or size sufficient to deliver both electroporation and electrolysis to the treatment site. The delivery of the combination electroporation and electrolysis by catheter may allow for a multitude of clinical applications, including nerve ablation, renal denervation, atrial fibrillation, arrhythmias, deep vein thrombosis, percutaneous transvascular applications, restenosis and other lumen based treatment sites. A catheter approach may also be utilized for the treatment of a variety of tumors accessible by catheter such as lung, liver, prostate, colon, bladder, rectal, and esophageal cancers. A catheter or needle approach could also be used for ablation of fat for cosmetic purpose.

Figure 6A:
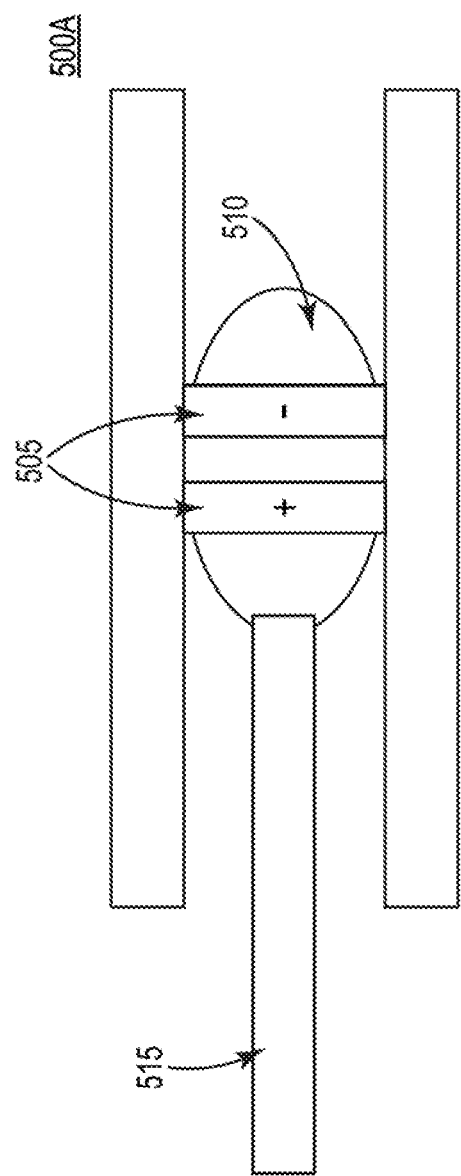
FIG. 6A is a schematic diagram of a balloon catheter according to an embodiment of the disclosure.
Figure 6B:
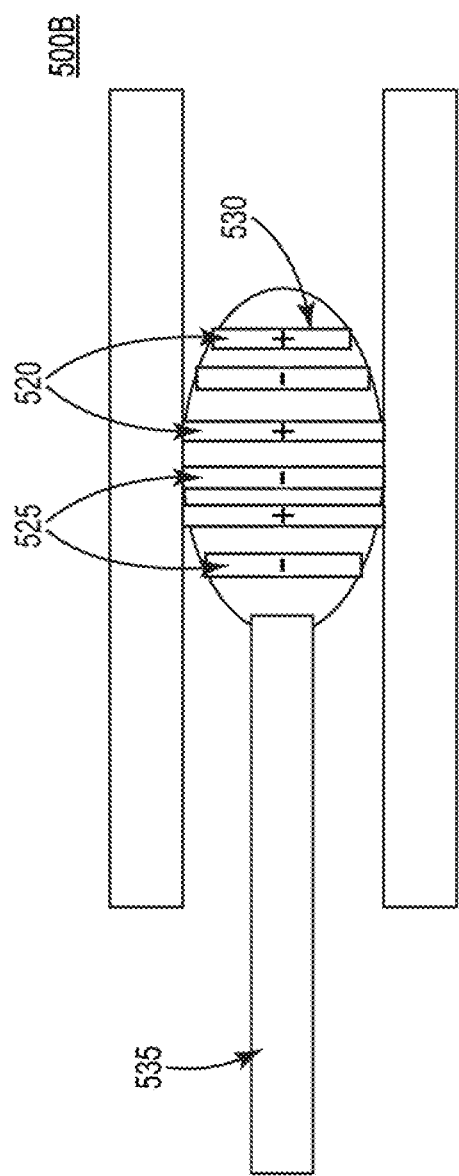
FIG. 6B is a schematic diagram of a balloon catheter according to an embodiment of the disclosure.

FIGS. 6A-B are schematic diagrams of balloon catheters 500A-B configured to provide electrolysis and electroporation treatment according to embodiments of the disclosure. Balloon catheter 500A includes electrodes 505 deposited on a balloon surface 510. The electrodes 505 are used to provide both electrolysis and electroporation. Balloon catheter 500B includes separate electrolysis electrodes 520 and electroporation electrodes 525 deposited on a balloon surface 530. In some embodiments, the electrodes 505, 520, 525 may be deposited on a catheter shaft 515, 535 in addition to or alternatively to the balloon 510, 530. The number, site and shape of the electrodes may be tailored for the specific treatment site.

Electrodes for electrolysis and/or electroporation may be integrated with other catheter designs. For example, spring electrodes that may be expanded and/or contracted may be used. In another example, electrodes may be integrated with a stent included with a catheter. In another example, electrodes may be integrated on the surface of a balloon having a ring shape. The ring-shape may allow the electrodes to contact a tissue surface, such as a blood vessel wall, while allowing a flow of material through the central portion of the ring. Other catheter designs may be used.

FIG. 7 is a schematic illustration of a multi-modality electrolysis device 600 according to an embodiment of the disclosure. In some embodiments, the multi-modality electrolysis device 600 may be used for the treatment of surface wounds and/or other tissue surfaces. The device 600 may include at least one electrode 610 and an aqueous matrix 605 in contract with the electrode. Generally, the electrode 610 and the aqueous matrix 605 may be selected such that electrolysis products are produced when a current is passed through the aqueous matrix 605 using the electrode 610. The electrode 610 may also deliver electroporation treatment. The electrode 610 and aqueous matrix 605 may be packaged for placement proximate the site to which delivery of electrolysis products and electroporation is desired. In FIG. 7, an electrode 610 and aqueous matrix 605 are shown packaged in a pad 615. In some embodiments, the pad 615 may include an adhesive strip 620 for securing the pad 615 to a desired site. Further examples of devices and pads that may be adapted for use with permeabilizing techniques are described in PCT Application Serial No. PCT/US2014/065783 filed Nov. 14, 2014, entitled "METHODS, SYSTEMS, AND APPARATUSES FOR DELIVERY OF ELECTROLYSIS PRODUCTS," which application is incorporated by reference herein in its entirety for any purpose.

In some embodiments, electrode 610 may include a plurality of electrodes. One or more electrodes may deliver electrolysis treatment and one or more electrodes may deliver electroporation treatment. The electrode 610 and/or a plurality of electrodes may include one or more materials. Electrode materials for electrolysis treatment are generally selected to include a material that is selected to produce the electrolysis products when a current is passed through the aqueous matrix 605 using the electrode 610. The materials chosen for the electrodes, including the electrode 610, may be chosen to produce certain the electrolysis products. For example, an anode may include iridium oxide and/or rubidium oxide deposited on titanium, which may improve the production of hypochlorous acid, and a cathode may include copper. The use of mixed metal oxide anode electrodes may produce different species of electrolysis products that may be tailored for different clinical needs. For example, platinum may be used if inert electrodes are desired or silver electrodes or silver/silver chloride, and/or copper electrodes if silver ions or copper ions are desired in the electrolytically produced solution, which may further enhance the tissue ablation effect. While metal ions produced by electrolysis from electrodes may enhance the tissue ablation effect of electrolysis they may also cause gene alteration or introduce toxic heavy metals in the body. Heavy metals may stay in the body for life, with detrimental effects. In contrast, when the products of electrolysis are those generated by the electrolysis of the ionic solution in tissue, these products may have a very short lifetime and may have no long term negative effect. Electroporation electrodes may include the same or different materials as electrolysis electrodes.

Although shown as a surface pad electrode 610 in FIG. 7, one or more electrodes may be implemented as a needle, a catheter, point electrode, other electrode configuration, and/or combination of configurations.

In some embodiments, electrodes may be separated by an insulating layer. The insulating layer may be implemented using any suitable insulating material. In some embodiments, the insulating layer between the electrodes may be omitted. In some embodiments, a portion of the aqueous matrix 605 is between the electrodes. In some embodiments, a portion of the aqueous matrix 605 is between the electrode 610 and the pad 615.

One or more of the electrodes in the device 600, such as the electrode 610 may be externally-accessible for receipt of an electronic signal from a controller (not shown), which may be placed remotely from the device 600. The controller may be implemented as controller 105 shown in FIG. 1. The controller may activate the electrode 610 and control the delivery of electrolysis treatment and electroporation treatment. The controller may control the magnitude and duration of each treatment type.

Apparatuses, devices, and systems described herein may include an aqueous matrix in contract with at least one electrode. The aqueous matrix 605 is shown in FIG. 7 in contact with electrode 610. Aqueous matrices described herein, including the aqueous matrix 605, may include components for forming electrolysis products. In some embodiments, the aqueous matrix 605 may be implemented using a gel and/or hydrogel. The aqueous matrix may include a saline solution. The aqueous matrix may have a pH selected to produce electrolysis products, such as hypochlorous acid. In some examples, the pH of the aqueous matrix 605 may range between 2 and 5. The aqueous matrix 605 may be placed in contact with a site for delivery of electrolysis products, such as by laying a pad including the aqueous matrix 605 on the site.

In some embodiments, the aqueous matrix 605 may include a low pH saline solution hydrogel (e.g. about 4 pH) that is configured for the production of hypochlorous acid. The materials included in the solution included in the aqueous matrix 605 may be chosen to produce the desired electrolysis products, such as hypochlorous acid). In some embodiments, the aqueous matrix 605 may have a higher electrical conductivity than the site for delivery of electrolysis products. The higher electrical conductivity of the aqueous matrix 605 may result in electrolysis products produced primarily in the aqueous matrix 605, not the tissue at the site. The ionic composition of the aqueous matrix 605 may be designed to have the desired conductivity but to include different ions from those normally in tissue, for example a greater concentration of Na or Ca. In some embodiments, the aqueous matrix 605 may be infused with a drug for combination therapy at the treatment site. That is, both the drug and electrolysis products are delivered to the treatment site. In some embodiments, the aqueous matrix 605 may be designed to have a desired conductivity and/or pH to enhance electroporation treatment.

In some embodiments, aqueous matrices described herein, such as the aqueous matrix 605, may be implemented using a liquid solution. The liquid solution may be prepared separately and applied directly to the treatment site before placement of a device, such as device 600. In some embodiments, the device 600 may be placed at the treatment site and the aqueous matrix 605 may be introduced to the treatment site by injecting it through a port (not shown) in the pad 615. In some embodiments, the pad 615 includes a dehydrated gel. Before use, the gel may be hydrated with a solution, such as saline, to form the aqueous matrix 605. In some embodiments, the aqueous matrix 605 is already present in the device 600.

The apparatuses, devices, and systems, such as treatment probes, catheters, and pads may all be used to deliver multimodality electrolysis. Other configurations, apparatuses, devices, and/or systems for delivering multimodality electrolysis may also be used. For example, one or more needle electrodes may be used in combination with an ultrasound transducer configured to provide sonoporation. Electrolysis treatment may also be combined with cryotherapy, thermal therapy, chemical therapy, and/or combinations thereof. For example a cryosurgery probe may also serve as one of the electrolysis electrodes.

Many clinical applications may benefit from the use of the combination of reversible electroporation and electrolysis. The reduced energy requirement and reduce treatment times may overcome limitations that previously discouraged the use of either electroporation or electrolysis regardless of the benefits of each on a stand-alone basis. The combination of both may overcome the limitations and enable a multitude of clinical uses.

For example ablation of nerves by the combination of electroporation and electrolysis include targeted lung denervation for chronic obstructive pulmonary disease, renal denervation and carotid body receptors for congestive heart failure.

The treatment of atrial fibrillation by the combination of reversible electroporation and electrolysis may be an enhanced treatment approach. The catheter delivery approach of the combination of reversible electroporation and electrolysis may allow for a low energy, non-thermal, fast treatment option. The ability to tailor the treatment application by electrode design also may allow the treatment to be configured to apply all elements of a full Cox procedure in a minimally invasive fashion.

Other vascular diseases may benefit from the combination treatment of electroporation and electrolysis. These include, but are not limited to, vascular lumen sites that are occluding like restenosis, peripheral artery disease, and deep vein thrombosis. Denervation for hypertension, cognitive heart disease and chronic obstructive pulmonary disease may benefit from the combination of electroporation and electrolysis.

The treatment of a variety of cancers by the combination of electroporation and electrolysis may be an enhanced treatment approach. The targeted treatment site may be accessed minimally invasively by either catheter or probe placement. The configuration of the device and the electrodes may deliver the combination of electroporation and electrolysis in an optimal manner for the targeted tumor. The types of tumors may include but are not limited to prostate, breast, lung, liver, brain, colon, esophagus, kidney, rectal, skin, stomach, pancreas, eye and uterine tumors.

The combination of electroporation and electrolysis may be an effective clinical approach for both malignant and benign tumor treatments. Thus benign tumor sites like Benign Prostatic Hypertrophy, fibroids and myomas may be treated.

Another area that may benefit from the combination of electroporation and electrolysis is the treatment of wound infections or parasite infection in tissue. Any area that requires sterilization of a wound could be treated by the combination of electroporation and electrolysis. The application of the combination of electroporation and electrolysis may be through catheter delivery, probe based or by a wound care pad that incorporates the ability to deliver both electroporation and electrolysis. Diseases like bedsores (pressure ulcers), venous ulcers or diabetic ulcers may be heated with the combination of reversible electroporation and electrolysis. Simple wounds that are pre infection may be treated preventatively with the combination of reversible electroporation and electrolysis. Surgical incisions may be treated with the combination of electroporation and electrolysis which may prevent infections from occurring. When surgical incisions develop an infection, the combination of electroporation and electrolysis may be used to treat it. Chronic wound infections, including the treatment of biofilm could be treated with the combination of electroporation and electrolysis.

A multitude of cosmetic applications may benefit from the combination of electroporation and electrolysis. They include but are not limited to skin resurfacing, skin tightening skin lesion removal, hair removal, wrinkle removal or reduction, and acne removal, reduction or prevention. Cosmetic applications can also be incorporated to treat unwanted area of the body, such as excess fat tissue ablation.

Another disease prevention approach includes the sterilization of foods such as meats by combination of reversible electroporation and electrolysis. The combination of both electroporation and electrolysis may be an improvement over either used individually for this purpose.

Those skilled in the art will recognize that the examples provided of both the design delivery systems and the clinical applications are not the limit of the uses of the combination of electroporation and electrolysis in the treatment of tissue. Many configurations of delivery systems exist, as well as applications that may benefit from the use of the discovery we disclose.

A variety of devices and or clinical applications can be made from a new method of combining sonoporation and electrolysis. For example, a wound care pad may be made that incorporates a gel and an electrode (ultrasound transducer sufficient to cause US waves to produce sonoporation) similar to the configuration of device 600 in FIG. 7. This new pad may improve wound care by both protecting the treatment area while applying both sonoporation and electrolysis product at the treatment site for optimal wound care disinfection. This device may be configured with a battery, connected to a generator or with an electrolytic cell design. The types of wounds this may be applied to include but are not limited to bed sores, diabetic ulcers, burns, tears, gashes, cuts, scrapes, irradiation and scars formation.

In another clinical application, the device may be a wound care dressing that may be applied over a large surface area. The wound care dressing may incorporate a gel coating and an electrode configuration. This device may be configured with a battery, connected to a generator or with an electrolytic cell. The wound care dressing may be applied to the treatment site. The sonoporation pulses may be delivered before or after the application of the electrolysis product. The electrolysis product may be diffused in the treatment area to disinfect the wound. The types of wounds that this may be applied to include but are not limited to bed sores, diabetic ulcers, burns, tears, gashes, cuts, scrapes, irradiation and scars formation.

In another clinical application the device may be a cosmetic patch that may be applied to the surface of the skin. The patch may be shaped to match the area of treatment. The patch may have a gel coating, transducer, and electrode configuration that delivers sonoporation pulses before or after optimized electrolysis product are applied. The combined sonoporation and electrolysis treatment may result in a controlled ablation of the skin surface or unwanted cosmetic feature. The healing process of this application may result in a tightening of the skin. This device may be configured with a battery, connected to a generator or with an electrolytic cell.

In another clinical application the device may be a cosmetic patch that may be applied to the surface of the skin to provide a controlled chemical peel. The patch may be shaped to match the area of treatment. The patch may have a gel coating, transducer, and electrode configuration that delivers sonoporation pulses before or after optimized electrolysis product are applied. The combined sonoporation and electrolysis treatment may result in the removal of dead layers of skin. The healing process of this application may result in a tightening of the skin. This device may be configured with a battery, connected to a generator, or with an electrolytic cell.

In another clinical application the device may be a cosmetic patch that may be applied to the surface of the skin to provide a controlled ablation of the skin surface or unwanted cosmetic feature. The patch may be shaped to match the area if treatment. The patch may have a gel coating, transducer, and electrode configuration that delivers sonoporation pulses before or after optimized electrolysis product are applied. The healing process of this application may result in a tightening of the skin. This device can be configured with a battery or with an electrolytic cell.

In another clinical application, surface based cancer sites may be treated with a combination treatment patch. The type of cancer sites to be treated includes but is not limited to benign skin tumors, actinic keratosis, basal cell carcinoma, dysplastic nevi, melanoma, and squamous cell carcinoma. The patch may deliver sonoporation to open the targeted cancer cells and the electrolysis process delivers a specific amount of electrolysis product to cause cell death. This device may be configured with a microcontroller and feedback system to determine the completeness of the treatment.

In another clinical application surface based skin growths or irregularities may be treated with a combination treatment patch. The type of skin growths or irregularities to be treated includes but is not limited to cysts, growths, lipomas, tags, acne, age spots, dark spots, wrinkles and warts. The patch may deliver sonoporation to open the targeted irregular cells and the electrolysis process delivers a specific amount of electrolysis product to cause cell death. This device may be configured with a microcontroller and feedback system to determine the completeness of the treatment.

Additional applications may involve the placement of the gel on the surface of a treatment area directly while placement of the electrodes creates the ability to form the electrolysis product at the site.

Another area that may benefit from the combination of sonoporation and electrolysis is the treatment of wound infections. Any area that requires sterilization of wound debridement could be treated by the combination of sonoporation and electrolysis. The application of the combination of sonoporation and electrolysis may be through catheter delivery, probe based or by a wound care pad that incorporates the ability to deliver both sonoporation and electrolysis. Diseases like bedsores, or diabetic ulcers can be treated with the combination of sonoporation and electrolysis. Simple wounds that are pre infection can be treated preventatively with the combination of sonoporation and electrolysis.

A multitude of cosmetic applications could benefit from the combination of sonoporation and electrolysis. They include but are not limited to skin resurfacing, skin tightening, skin lesion removal, hair removal, wrinkle removal or reduction, and acne removal, reduction or prevention. Cosmetic applications can also be incorporated to treat unwanted area of the body, such as excess fat tissue.

Another disease prevention approach includes the sterilization of foods such as meats by combination of sonoporation and electrolysis. The combination of both sonoporation and electrolysis may be an improvement over either used individually for this purpose.

Another embodiment may include the combination of sonoporation and electrolysis in a surgical probe. The probe may have a tip that incorporates electrodes and transducer elements capable of delivering sonoporation and electrolysis to a treatment site. The treatment site may be at the surface of a patient or inside a surgical cavity. The probe may be used to sterilize a treatment site. The probe may be used to debride a wound site. The probes may be inserted into the body to treat an unwanted area such as fatty tissue.

Another embodiment may utilize a method to control the dose the amount of electrolysis product produced and applied to the treatment site. A delivery device may be used to apply the electrolysis product produced at the time of application. For example a wound care pad may be configured to produce a specific amount of electrolysis product. The wound care pad may be the delivery system that may ensure the application of the electrolysis product is done in a controlled fashion, such that the electrolysis product is in place for the duration of the treatment. The wound care pad may incorporate an electrode design that facilitates the optimal production of electrolysis products. The electrodes may be connected to a DC power source. The power source may be controlled by a controller so that its output is constant, pulsed, or other modulated pattern for a specific period of time or all the time. The wound care pad may also incorporate a gel pack filled with a solution or hydrogel. The amount of gel is designed to produce a specific amount of electrolysis product over a period of time with a specific amount of energy in coulombs applied. The gel may be housed in protective pack that is broken prior to application on the wound. The breaking of the protective pack allows for the gel to come into contact with the electrodes on the wound pad. Alternatively, a dry pad that is produced from a saline or other optimized electrolysis environment product can be used as a way to introduce control in the electrolysis product production.

A variety of devices and or clinical applications may be made from a method of combining, freezing and cold, and electrolysis. Cryosurgery is a tissue ablation method that generally employs one or more probes, insulated except at the metal tip, to freeze and thereby ablate undesirable tissues. One of the advantages of cryosurgery may be that the extent of freezing may be monitored in real time with medical imaging techniques, such as ultrasound. However, in the temperature range of from 0 C to about −20 C some cells may survive freezing and therefore, the extent of freezing, as seen by medical imaging, does not necessarily correspond to the extent of cell death. Pores and defects may open in the cell membrane in the temperature ranges below the phase transition temperature for lipids, about +15 C, with the defect formation increasing down to subzero freezing temperatures. Furthermore, during freezing, the solutes in tissue may be rejected and concentrated between the ice crystals. These properties of cryosurgery may be combined with electrolysis, which may enhance the cell death from that of cryosurgery and electrolysis alone.

For example, cryosurgery and electrolysis may be combined using a system, such as the system shown in FIG. 1. The un-insulated metal tip of a cryosurgery probe may serve as one of the electrodes of the electrolysis device 115. Connecting the un-insulated tip to the power supply 120 may generate products of electrolysis, prior to the delivery of cold and freezing. The extent of electrolysis may be determined from treatment planning or measurements with the pH meter 125. When these show that the desired electrolytic front has reached a desired location, the cryosurgery probe may be connected to a cooling system (not shown in FIG. 1) and freezing begins. Freezing may continue until the ice front interface reaches the desired extent of ablation, as shown by imaging monitoring, e.g. ultrasound. The ice front may be at a temperature of −0.56 C and the temperature drops through the ice lesion to the temperature of the cryo-probe. As indicated earlier the process of cooling and freezing may open and permeabilize the cell membrane, while the process of freezing causes a concentration of the solutes in the freezing solution, including an increase in the concentration of the products of electrolysis. The permeabilization of the cell membrane and the increased concentration of products may introduce the products of electrolysis into cells and induce, after thawing, cell death throughout the entire frozen region, including in the temperature range in which cells usually survive freezing. This may facilitate cell ablation by cryosurgery to the freezing interface as monitored by imaging, which may improve the accuracy and the effectiveness of cryosurgery.

The combination of permeabilization by cold and/or freezing and electrolysis may be used for all the current applications of cryosurgery, such as treatment of tumors, vascular treatment, ablation of fat in cosmetic surgery by cold alone, or by, cold and freezing, treatments in dermatology and cosmetics. The treatment of a variety of tumors by the combination of cryosurgery and/or cold and electrolysis may be an enhanced treatment approach. The targeted treatment site may be accessed minimally invasively by either catheter or probe placement. The configuration of the device and the electrodes may deliver the combination of cryosurgery or cold and electrolysis in an optimal manner for the targeted tumor. The types of tumors may include but are not limited to prostate, breast, lung, liver, brain, colon, esophagus, kidney, rectal, skin, stomach, pancreas, eye and uterine tumors.

The combination of cryosurgery or cold and electrolysis may be an effective clinical approach for both malignant and benign tumor treatments. Thus benign tumor sites like Benign Prostatic Hypertrophy, fibroids and myomas may be precisely treated under medical imaging monitoring.

In some embodiments, one or more treatment probes and/or electrodes may be integrated into a cryosurgery ablation catheter. The electrodes for delivering the treatments may be in any combination, shape or size sufficient to deliver both cryosurgery and electrolysis to the treatment site. The metal un-insulated part of the cryosurgery catheter may be used as at least one electrolysis electrode. The second electrode may also be on the catheter or in a remote location, including on the surface of the body. The delivery of the combination cryosurgery and electrolysis by catheter may allow for a multitude of clinical applications, including nerve ablation, renal denervation, atrial fibrillation, arrhythmias, deep vein thrombosis, percutaneous transvascular applications, restenosis and other lumen based treatment sites. A catheter approach may also be utilized for the treatment of a variety of tumors accessible by catheter such as lung, liver, prostate, colon, bladder, rectal and esophageal cancers. Other vascular diseases may benefit from the combination treatment of cryosurgery and electrolysis. These include, but are not limited to, vascular lumen sites that are occluding like restenosis, peripheral artery disease, and deep vein thrombosis. Denervation for hypertension, cognitive heart disease and chronic obstructive pulmonary disease would benefit from the combination of electroporation and electrolysis.

A catheter or needle approach could be also used with the combination freezing, and/or cold and electrolysis for ablation of fat for cosmetic purpose.

Other cosmetic applications of the combination cryosurgery, cooling and electrolysis include but are not limited to skin resurfacing, skin tightening, skin lesion removal, hair removal, wrinkle removal or reduction, and acne removal, reduction or prevention.

Other applications include various areas of dermatology. The type of cancer sites to be treated on the skin includes but is not limited to benign skin tumors, actinic keratosis, basal cell carcinoma, dysplastic nevi, melanoma, and squamous cell carcinoma.

Some specific experimental examples are provided below to facilitate appreciation of embodiments described herein. The experimental examples presented are not intended to be comprehensive or exhaustive of all experiments performed or of all results obtained.

EXAMPLE I

According to a first non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder, similar to the electrode configuration shown in FIG. 5A. Graphite was used to avoid contamination of the gel with metal ions. The electrodes were connected to a constant voltage power supply or to a BTX electroporation (Harvard Instruments) electroporator. The distance between the electrodes was 10 mm. Changes in color near the electrodes were observed due to electrolysis induced change in pH.

The first experiment involved the delivery of typical electroporation pulses of 1000 V between the electrodes. One hundred microsecond long pulses at a frequency of 1 Hz in groups of 99 pulses were delivered. Between groups of pulses, a two minute rest period was used to let the system cool.

The gel exhibited a stained region after 99 pulses. The stained region surrounded the electrodes and was not continuous, confirming the delivery of electrolysis products. However, the extent of the stain did not cover the treated tissue to the isoelectric field of 200 Vcm or 100 V/cm line, produced by the 1000 V electroporation pulses. In typical irreversible electroporation protocols used in current clinical applications for tissue ablation, fewer than 100 pulses are used. Under these typical conditions there are no electrolysis products in the region of electric fields of 100 V/cm or 200 V/cm. 200 V/cm and 100 V/cm are reversible electroporation fields that do not cause cell death in the absence of electrolytic products.

After three sequences of 99 pulses, a substantial volume of gel in the treated region has been affected by the products of electrolysis and has changed the pH of the gel. However, even after 3×99 pulses, the region affected by electrolysis has not yet reached the 100 V/cm isoelectric field line. The region affected by the anode was larger than that affected by the cathode. In addition, in the center of the region stained near the anode there was a white discolored circle. This may be due to a typical effect of electrolysis. In electrolysis there is an electro-osmotic driven flow of water from the anode to the cathode. This is a well-known phenomenon. This phenomenon may be used to generate flows in tissue during electrolysis in desirable directions. Furthermore, by adding electrolysis products by extending electrolysis treatment and/or introducing a solution configured for electrolysis product production, the treated zone may be substantially expanded.

EXAMPLE II

According to a second non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder, similar to the configuration shown in FIG. 5A. Graphite was used to avoid contamination of the gel with metal ions. The electrodes were connected to a constant voltage power supply or to a BTX electroporation (Harvard Instruments) electroporator. The distance between the electrodes was 10 mm. Changes in color near the electrodes were observed due to electrolysis induced change in pH.

The second experiment involved the delivery of typical electroporation pulses of 500 V between the electrodes. One hundred microsecond long pulses at a frequency of 1 Hz in groups of 99 pulses were delivered. Between groups of pulses, a two minute rest period was used to let the system cool.

The pH affected area after three pulse sequences of 99 pulses and a voltage between electrodes of 500 V is smaller than when the pulse was of 1000 V.

EXAMPLE III

According to a third non-limiting example, a Petri dish was used to cast an agar gel made of physiological saline with a pH dye. The pH dye was 5% pH indicator (RC Hagen wide range). The pH indicator vas added to the agar gel phantom before its solidification. Two 0.9 mm graphite electrodes were inserted into the gel through a holder, similar to the configuration shown in FIG. 5A. Graphite was used to avoid contamination of the gel with metal ions. The electrodes were connected to a constant voltage power supply or to a BTX electroporation (Harvard Instruments) electroporator. The distance between the electrodes was 10 mm.

The DC power supply applied a voltage of 10 V (a current of 60 mA) between the electrodes. It was evident that after 168 seconds the pH dye area marked as affected by electrolysis products from direct current was much larger than the area affected by electrolysis products generated by electroporation pulses in Examples I and II. The pH change affected area was sufficiently large so that a 1000 V pulse applied between the electrodes may ablate to the isoelectric field line of 100 V/cm. 100 V/cm is considered reversible electroporation and permeabilization of the cell membrane is typically done with eight pulses. Cells survive exposure to electric fields of eight, 100 V/cm. However, when electrolytic products are generated in sufficient quantity to diffuse to the 100 V/cm isoelectric-field lines, the cells exposed to eight 100 V/cm electric fields do not survive. Therefore, it appeared that a preferential way to use the combination of electrolysis/electroporation for tissue ablation is to use conventional electrolysis with relatively (compared to electroporation) long DC currents at low voltage and current for the products of electrolysis to diffuse through the targeted volume in combination with several high field electroporation type pulses that are sufficient to permeabilize the cell membrane. There may be several possible combination protocols with electrolysis type currents and electroporation type pulses delivered in various sequences and configurations. For instance: electrolysis first, electroporation later or electroporation first electrolysis later, or electroporation first, electrolysis second and electrolysis again third or at different intervals in time between electrolysis and electroporation.

EXAMPLE IV

According to a fourth non-limiting example, a Petri dish was used to cast an agar gel made of physiological saline with a pH dye. The pH dye was 5% pH indicator (RC Hagen wide range). The pH indicator was added to the agar gel phantom before its solidification. Two 0.9 mm graphite electrodes were inserted into the gel through a holder, similar to the configuration shown in FIG. 5A. Graphite was used to avoid contamination of the gel with metal ions. The electrodes were connected to a constant voltage power supply or to a BTX electroporation (Harvard Instruments) electroporator. The distance between the electrodes was 10 mm.

A voltage of 5 V was applied across the electrodes with a current of 9 mA. Staining indicated that this produced a comparable outcome to electrolytic treatment with 10 V in Example III and is also suitable for tissue electrolysis/electroporation ablation protocol described in Example III. The center of the stained gel near the anode was discolored because of the water electromigration effect.

EXAMPLE V

Conventional tissue ablation by electroporation is delivered using two electrodes. The electrodes are positioned relatively close to each other to facilitate high electric fields with reasonable voltages. It may be advantageous to ablate tissue by electroporation in a modality similar to radiofrequency thermal ablation, i.e. one electrode in the center of the undesirable tissue and a second electrode remotely, similar to the electrode configuration shown in FIG. 5B. However, a problem with this configuration may be that for a single needle or point active electrodes with a remote second electrode, the electric field near the needle or point electrode descends very rapidly with distance from the electrode. In the case of the needle electrode, as one over the distance square and in the case of a point electrode, as one over the distance to the third power. Consequently the extent of tissue affected by irreversible electroporation is small.

According to a fifth, non-limiting example, a typical one dimensional in cylindrical coordinates needle electrode was used. The central electrode was 0.9 mm graphite and the second electrode was a lining of copper around the wall of a Petri dish. The Petri dish was used to cast an agar gel made of physiological saline with a pH dye. The pH dye was 5% pH indicator (RC Hagen wide range). The pH indicator was added to the agar gel phantom before its solidification.

A sequence of electrolysis/electroporation treatment was applied with a single central needle. The sequence started with electrolysis in which 10 V, and 200 mA were induced between the electrodes. Two sets of experiments were performed one set with the anode in the center and one set with the cathode in the center. The gel was observed after 45 seconds, 90 seconds, 120 seconds after start of electrolysis. Staining was observed around the electrode in both sets of experiments after 45 seconds, and the stained area continued to increase as time went on. The amount of electrolysis products observed in this set of experiments was significantly higher than for the case of two adjacent electrodes at the same voltage in the previous examples. The reason may be that the current was higher and/or possibly because the products from the anode and cathode do not interact with each other due to the increased distance. These experiments suggest that it may be advantageous to generate the electrolysis products from a central electrode with a distant second electrode. First the amount of electrolysis products appears to be higher and the composition appears to be better defined. It may be preferable when two electrodes are used for electroporation to use one or both of these electrodes with one polarity and another remote electrode with another polarity for generating electrolysis products in some applications.

EXAMPLE VI

According to a sixth non-limiting example, a typical one dimensional in cylindrical coordinates needle electrode was used. The central electrode was 0.9 mm graphite and the second electrode was a lining of copper around the wall of a Petri dish. The Petri dish was used to cast an agar gel made of physiological saline with a pH dye. The pH dye was 5% pH indicator (RC Hagen wide range). The pH indicator was added to the agar gel phantom before its solidification. Three sets of 1000 V, 100 microsecond long 1 Hz frequency, 99 pulses per set were delivered between the central electrode and the electrode around the Petri dish.

It was observed that after the delivery of three sets of 99 pulses, with 1000 V electroporation type pulses, the amount of electrolysis products generated is negligible relative to that produced by DC electrolysis in the previous examples. The isoelectric field lines which are associated with irreversible electroporation, above about 400 V/cm were much closer to the central electrode than the isoelectric lines of 100 V/cm. Therefore, the extent of tissue ablation with irreversible electroporation alone, which reached only the about 400 V/cm isoelectric field line, was much smaller than the extent of tissue ablation with the combination electrolysis and electroporation, which reached the isoelectric field line of 100 V/cm.

From Examples V and VI, it is observed that when a central electrode and a remote electrode are used for tissue ablation around the central electrode, combining electrolysis with electroporation may substantially expand the region of tissue ablation near the central electrode over electroporation alone. The various combinations of electrolysis and electroporation sequences discussed earlier for two needle electrodes may be valid for a central needle electrode also.

The examples provided are for explanatory purposes only and should not be considered to limit the scope of the disclosure.

Those skilled in the art will recognize that the examples provided of both the design deliver systems and the clinical applications are not the limit of the uses of the combination of electroporation and electrolysis. Many configurations of delivery systems exist, as well as applications that would benefit from the use of the discovery we disclose.

It is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present devices, apparatuses, systems, and methods and should not be construed as limiting the appended claims to any particular embodiment or group of embodiments. Thus, while the present disclosure has been described in particular detail with reference to exemplary embodiments, it should also be appreciated that numerous modifications and alternative embodiments may be devised by those having ordinary skill in the art without departing from the broader and intended spirit and scope of the present disclosure as set forth in the claims that follow. Accordingly, the specification and drawings are to be regarded in an illustrative manner and are not intended to limit the scope of the appended claims.

What is claimed is:

1. A method for tissue ablation, the method comprising:
   permeabilizing cell membranes in the tissue; and
   performing electrolysis to generate products of electrolysis in the tissue.

2. The method of claim 1 wherein said permeabilizing occurs before, during, or after said performing electrolysis, or combinations thereof.

3. The method of claim 1 wherein said permeabilizing comprises performing electroporation, cryosurgery, freezing, cold-poration, heat-poration, sonic-poration, chemoporation or combinations thereof.

4. The method of claim 1, further comprising applying an aqueous solution to the tissue.

5. The method of claim 1, wherein said performing electrolysis comprises applying an electrode to the tissue and providing an electrical signal to the electrode.

6. The method of claim 1, further comprising:
   measuring a pH in the tissue; and
   stopping performing electrolysis when the measured pH reaches a desired level.

7. The method of claim 1, further comprising measuring at least one of an electric field, a current, a voltage, or a resistance in the tissue.

8. The method of claim 1, wherein permeabilizing and performing electrolysis comprise applying an electric field of at least 100 V/cm.

9. The method of claim 8, wherein the electric field is applied for a period of time that is equal or less than 30 minutes.

10. The method of claim 1, wherein permeabilizing includes applying an electric field of at least 100 V.

11. The method of claim 10, wherein the electric field is applied for a period of time equal or less than 168 seconds.

12. The method of claim 1, wherein performing electrolysis includes applying a direct current of at least 9 mA.

13. The method of claim 12, wherein the direct current is applied for a period of time equal or less than 20 minutes.

14. The method of claim 1, wherein permeabilizing comprises reducing a temperature of the tissue to less than or equal to −0.56 C.

15. The method of claim 1, wherein permeabilizing comprises reducing a temperature the tissue to equal to or greater than −0.56 C, wherein the tissue does not freeze at the temperature.

16. An apparatus for tissue ablation, the apparatus comprising:
   an electrolysis device configured to generate products of electrolysis in the tissue; and
   a permeabilization device configured to permeabilize cell membranes in the tissue.

17. The apparatus of claim 16, wherein the permeabilization device comprises an electroporation device, a sonicator, a cryosurgery device, or a combination thereof.

18. The apparatus of claim 16, wherein the electrolysis device comprises at least one electrode.

19. The apparatus of claim 18 wherein permeabilization device includes the at least one electrode of the electrolysis device.

20. The apparatus of claim 16, the apparatus further comprises a pH meter to monitor pH in the tissue.

21. The apparatus of claim 16, further comprising an electric meter to monitor at least one of an electric field, a current, a voltage, or a resistance in the tissue.

22. The apparatus of claim 16, further comprising a control configured to provide an electrical signal to at least one of the electrolysis device or the permeabilization device.

23. The apparatus of claim 16, further comprising a power supply coupled to at least one of the electrolysis device or the permeabilization device.

24. The apparatus of claim 16, wherein the permeabilization device includes a cooling system.

* * * * *